United States Patent
Pressacco et al.

(10) Patent No.: US 8,454,705 B2
(45) Date of Patent: Jun. 4, 2013

(54) PROSTHETIC ELEMENT AND RELATIVE METHOD TO MAKE IT

(75) Inventors: Michele Pressacco, Udine (IT); Gabriele Lualdi, Fagagna (IT); Paolo Dalla Pria, Udine (IT)

(73) Assignee: Limacorporate SpA, San Danielle del Friuli (UD) (IT)

( * ) Notice: Subject to any disclaimer, the term of this patent is extended or adjusted under 35 U.S.C. 154(b) by 339 days.

(21) Appl. No.: 12/601,510

(22) PCT Filed: May 29, 2008

(86) PCT No.: PCT/IB2008/001354
§ 371 (c)(1),
(2), (4) Date: Mar. 17, 2010

(87) PCT Pub. No.: WO2008/146141
PCT Pub. Date: Dec. 4, 2008

(65) Prior Publication Data
US 2010/0191345 A1    Jul. 29, 2010

(30) Foreign Application Priority Data
May 29, 2007   (IT) .............................. UD2007A0092

(51) Int. Cl.
*A61F 2/34*   (2006.01)
(52) U.S. Cl.
USPC ...................................................... 623/22.33
(58) Field of Classification Search
USPC ...................................................... 623/22.33
See application file for complete search history.

(56) References Cited

U.S. PATENT DOCUMENTS

| | | | |
|---|---|---|---|
| 4,636,219 A | | 1/1987 | Pratt et al. |
| 4,715,860 A | * | 12/1987 | Amstutz et al. ............ 623/22.33 |
| 4,769,041 A | | 9/1988 | Morscher |
| 4,944,817 A | | 7/1990 | Bourell et al. |
| 4,976,738 A | | 12/1990 | Frey et al. |
| 5,108,435 A | | 4/1992 | Gustavson et al. |
| 5,156,625 A | * | 10/1992 | Marchetti et al. .......... 623/22.33 |
| 5,443,510 A | | 8/1995 | Shetty et al. |
| 5,711,960 A | | 1/1998 | Shikinami |
| 6,312,473 B1 | * | 11/2001 | Oshida ....................... 623/23.55 |
| 2004/0191106 A1 | | 9/2004 | O'Neill et al. |
| 2006/0147332 A1 | | 7/2006 | Jones et al. |
| 2007/0141111 A1 | * | 6/2007 | Suokas et al. ................. 424/426 |

FOREIGN PATENT DOCUMENTS

DE        196 14 949 A1    10/1997
DE     20 2006 015416      11/2006

(Continued)

*Primary Examiner* — Bruce E Snow
*Assistant Examiner* — Melissa Hoban
(74) *Attorney, Agent, or Firm* — Novak Druce Connolly Bove + Quigg, LLP

(57) ABSTRACT

Prosthetic element including a metal cap having inside an acetabular seating and method to make it. At least part of the cap is a lattice having open and intercommunicating cavities. At least part of the lattice is formed, without a continuity break, by geometric meshes of polygonal shape repeated in space over all or part of the body, having a cellular geometry with elementary cells open and contiguous, to define a plurality of polygons with spatial development delimiting the cavities. Each geometric mesh has a first polygonal part with four sides, each of the sides being an angled segment, and a second part being an angled segment and a third part being an angled segment. Each angled segment has first and second consecutive rectilinear segments forming an angle at an intersection of each pair of its first and the second consecutive segments. The first polygonal part has non co-planar vertexes.

24 Claims, 4 Drawing Sheets

FOREIGN PATENT DOCUMENTS

| | | |
|---|---|---|
| EP | 0 623 687 A2 | 11/1994 |
| FR | 2 685 192 A1 | 6/1993 |
| GB | 2 059 267 A | 4/1981 |
| WO | 99/62438 A1 | 12/1999 |
| WO | 2005/018698 A1 | 3/2005 |
| WO | 2006/125711 A1 | 11/2006 |

* cited by examiner

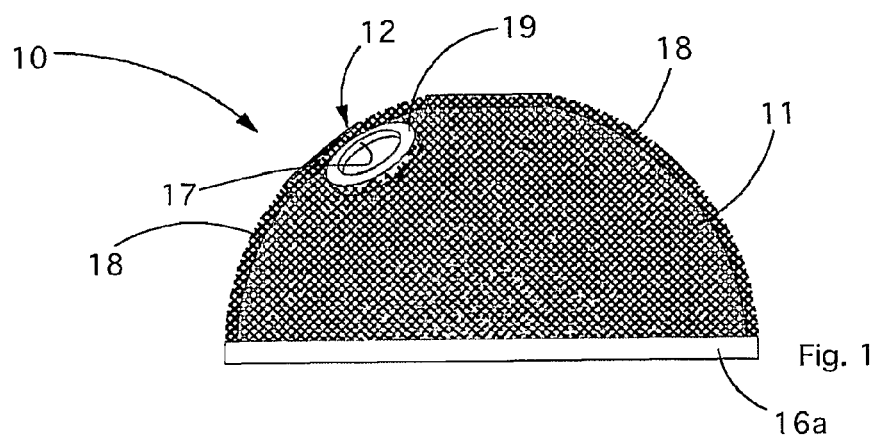
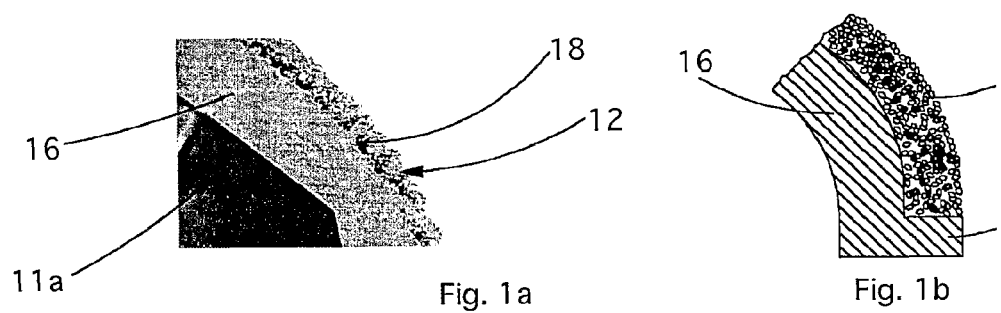
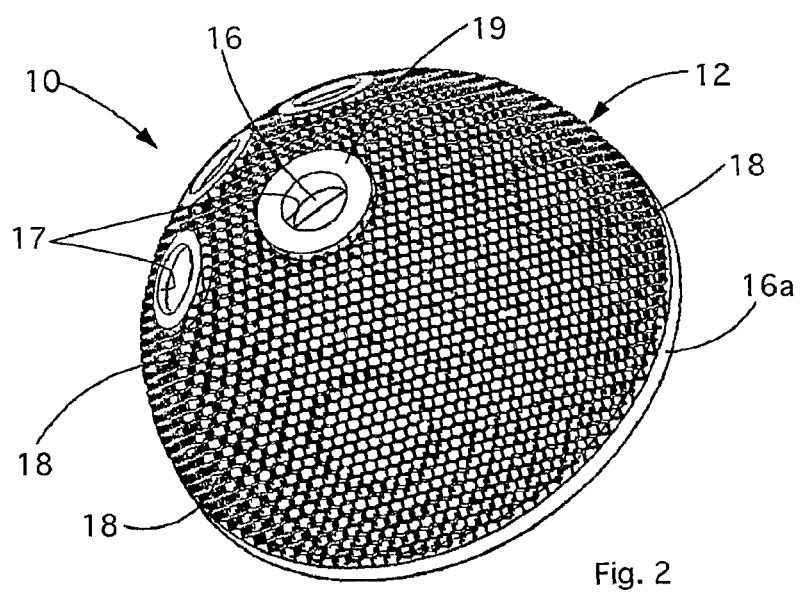

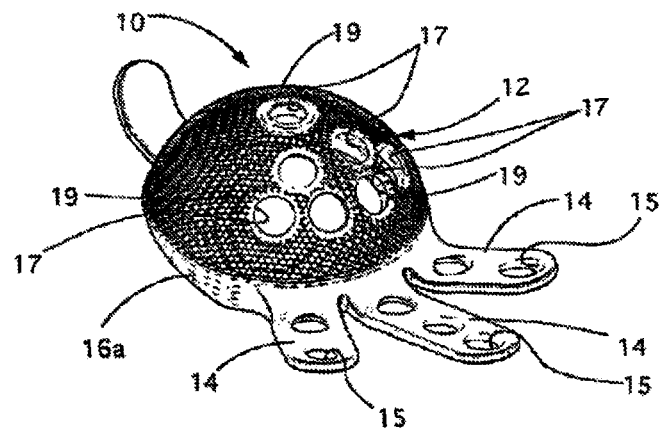
Fig. 3
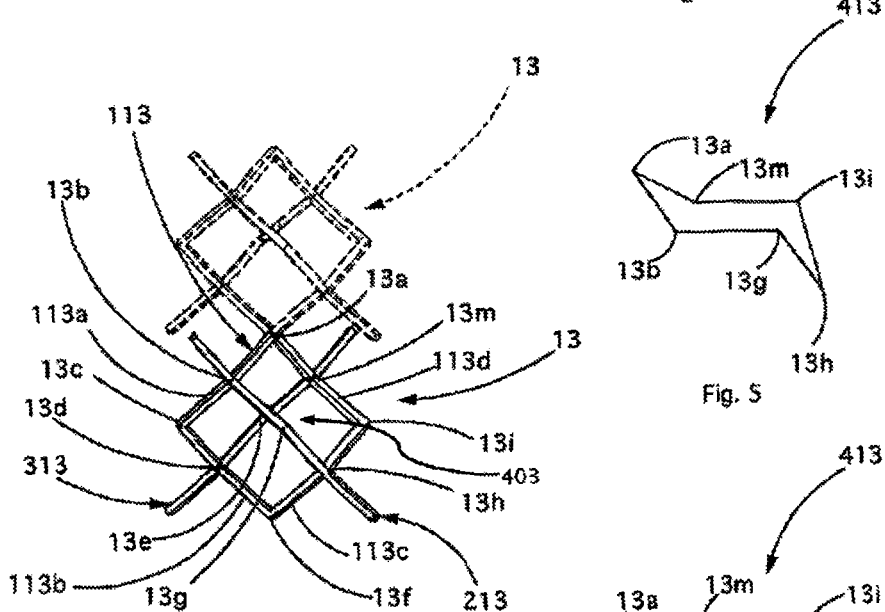
Fig. 4
Fig. 5
Fig. 6

PROSTHETIC ELEMENT AND RELATIVE METHOD TO MAKE IT

FIELD OF THE INVENTION

The present invention concerns a prosthetic element with a cellular structure, and the relative method to make it, usable preferably but not only in prostheses intended to restore femoral articulation.

The invention is applied in the medical field of bone prostheses implants and bone substitutes.

BACKGROUND OF THE INVENTION

Acetabular cups are known, substantially spherical in shape, intended to replace or reinforce the natural acetabular cavity to accommodate the head of the relative femoral prosthesis. Acetabular cups, generally made of metal, can be advantageously covered with porous materials in order to improve the process of osteo-integration with the bone tissue of the pelvis.

Generally, materials commonly used to make the covering for acetabular cups consist of powdered titanium or hydroxyapatite. These materials are usually made to adhere to the external surface of the acetabular cup by means of the plasma-spray technique, or with welded metal nets or by means of small balls applied at high temperature.

Prosthetic elements are known, of the type in question, which have a solid and compact internal body, whereas in the external part a lattice is made which covers the acetabular cup. The lattice is applied on, or distanced from, the external wall of the cup.

One of the methods used is DMSLS (Direct Metal Selective Laser Sintering). This method allows to make products and components of metal material with a process, using laser rays, that solidifies successive layers of powdered metal material of pre-defined thickness. Each of said layers is representative of a horizontal section, of pre-defined thickness, of the three-dimensional model of the product.

Another technique is EBM (Electron Beam Melting), which allows to make components, for example of titanium, starting from a bath of titanium powder, by means of a melting process under conditions of high vacuum, and solidification of successive layers as in the DMSLS technique described above.

These techniques allow to reach great precision and to achieve the desired structures.

Purpose of the present invention is therefore to achieve, with one of the known techniques or an equivalent technique, a prosthetic element with a cellular structure made in a single piece such as to promote bone re-growth and good anchorage of the prosthesis.

The Applicant has devised, tested and embodied the present invention to overcome the shortcomings of the state of the art and to obtain these and other purposes and advantages.

SUMMARY OF THE INVENTION

The present invention is set forth and characterized in the independent claims, while the dependent claims describe other characteristics of the invention or variants to the main inventive idea.

In accordance with the above purpose, a prosthetic element with cellular structure according to the present invention is usable in particular, but not only, as an acetabular cup for a bone prosthesis in implant operations in the pelvic acetabulum. The prosthetic element is able to accommodate a prosthetic head or an insert for an acetabular cup into which, in turn, the head of a femoral prosthesis is inserted.

According to one characteristic of the present invention, the prosthetic element comprises a cap made of metal material, having an acetabular seating inside.

The cap has an internal wall which lines the seating and an external part consisting of a lattice of cells achieving a plurality of cavities, disposed three-dimensionally, open and intercommunicating, connected with each other.

The lattice is solid with the part facing toward the outside of the internal wall.

According to the present invention, at least part of the lattice is formed, without a break in continuity, by one or more models of a plurality of geometric meshes which are repeated spatially over all or part of the body of the prosthetic element, having a cellular geometry with open and contiguous elementary cells, so as to define a plurality of polygons with a spatial development delimiting the cavities, so that the lattice is able to promote osteo-integration.

According to a variant solution, the internal wall is made of compact material.

According to another solution, the internal wall is made as a lattice of cells.

According to one embodiment of the present invention, the lattice has at the lower part a base layer, for example, but not restrictively, which may or may not be annular, compact, or in physical continuity with the internal wall.

According to a variant, the geometric meshes all have the same shape and size, varying their disposition in the lattice. In this way, the polygons that are defined are equal and repeated spatially with varying orientation, according to needs.

According to another form of embodiment, the geometric meshes are denser, therefore they have a smaller size, in proximity with the zone that makes up the internal wall.

With the present invention, the empty spaces and cavities that are created in the three-dimensional lattice are achieved according to a desired, statistical or random distribution, in any case able to reproduce bone porosities, reproducing a three-dimensional succession of cavities, variously adjacent to each other, without a break in continuity, and which do not define interstices, passages, canaliculi, meati or other similar preferential paths open in the volume between the internal wall and the external surface of the lattice. This solution determines an optimum osteo-compatibility and uniform re-growth of the bone, also because it can be designed on each occasion according to the purposes proposed.

According to a variant, each geometric mesh is polygonal in shape with vertexes that are not co-planar, and the open free area of each elementary cell has an equivalence to a circle with a diameter comprised in a range from about 0.3 mm to about 1.5 mm.

According to another variant, each geometric mesh is formed by a first polygonal part with sides formed by angled segments and by a second and third part with an angled segment.

The first polygonal part can be substantially quadrangular in shape.

According to one embodiment of the present invention, the second and third part with the angled segment can be disposed crossed with respect to each other, superimposed over the first part, one on one side and the other on the other side of the first part, so as to define, in space, a plurality of hexagons having the vertexes which are not co-planar.

According to a variant, each geometric mesh defines four hexagons with spatial development.

According to another variant, the cap has a plurality of holes, typically for attachment to the bone, which are delimited along the perimeter by a portion of compact material, with the advantage that it reinforces the local structure in view of the attachment to the bone.

The prosthetic element is obtained, with one or another of the EBM (Electron Beam Melting) technique or DMSLS (Direct Metal Selective Laser Sintering) technique, or an equivalent technique, by depositing and solidifying successive plane layers of determinate and limited thickness of powdered metal material. The sequence of the layers gradually achieves the relative three-dimensional theoretical model, generated by means of design instruments for electronic processors, of the prosthetic element according to the present invention and, at the same time, creates the desired cellular lattice.

A preferential solution of the present invention provides that the lattice possesses a cellular geometry with open cells. According to this solution, the vacuum generated by the geometrical figure is selected so as to guarantee optimum conditions of integration and bone re-growth on the external surface of the prosthetic element.

The lattice therefore guarantees the prosthetic element a high level of porosity. The prosthetic element according to the invention is able to support the normal physiological loads both in the short term and in the long term, with a degree of rigidity totally comparable with usual prostheses.

According to a variant, the prosthetic element according to the present invention is made of titanium alloy or other alloy materials, by virtue of their properties, including bio-compatibility.

The present invention also concerns a method to make a prosthetic element with an open cellular structure comprising a cap advantageously made of metal material with a body at least partly consisting of a three-dimensional lattice. The three-dimensional lattice thus defined creates a plurality of intercommunicating cavities.

The method according to the present invention uses at least a step in which, by means of the Electron Beam Melting technique, or by means of the Direct Metal Selective Laser Sintering technique, or an equivalent technique, plane, discontinuous layers of powdered metal material are deposited and made to solidify. Each of the layers defines a figure obtained by sectioning the three-dimensional model of the lattice and, at the same time, of the prosthetic element.

In particular, the prosthetic element is obtained by successive, continuous, parallel, adjacent and solid layers so as to constitute an internal wall of the cap which lines the seating, and at least part of the external part of the cap is obtained in physical continuity with every single layer.

The layers that make up the external part are coordinated in proportion to a predetermined final figure, in which the plurality of layers is obtained in a discontinuous form so as to determine a lattice with cells achieving a plurality of cavities, disposed three-dimensionally, open and intercommunicating, connected with each other, the lattice being achieved in physical continuity with the part facing towards the outside of the compact internal wall.

According to one embodiment, a base layer is obtained, for example, but not restrictively, of annular shape, with compact cells.

According to another embodiment, the lattice is obtained in physical continuity with the internal wall and without a break in continuity, achieving one or more models of a plurality of geometric meshes which are repeated in space on all or part of the body of said prosthetic element, having a cellular geometry with open and contiguous elementary cells, so as to define a plurality of polygons with a spatial development delimiting the cavities, so that the lattice is able to promote osteo-integration.

According to a variant embodiment, in the step of making the individual layers, the lattice is defined in its periphery according to an open and desired cellular structure in order to achieve the geometric meshes with a cellular geometry with elementary cells open and contiguous of a polygonal shape with vertexes which are not co-planar, in which the open free area of each elementary cell has an equivalence to a circle with a diameter comprised in a range from about 0.3 mm to about 1.5 mm.

BRIEF DESCRIPTION OF THE DRAWINGS

These and other characteristics of the present invention will become apparent from the following description of some preferential forms of embodiment, given as a non-restrictive example with reference to the attached drawings wherein:

FIG. 1 is a front view of a prosthetic element according to the present invention;

FIG. 1a is an enlarged section of part of the prosthetic element in FIG. 1;

FIG. 1b is another enlarged section of part of the prosthetic element in FIG. 1;

FIG. 2 is a three-dimensional view of the prosthetic element in FIG. 1;

FIG. 3 is a three-dimensional view of a variant of the prosthetic element according to the present invention;

FIG. 4 is an enlarged detail of a lattice with a model of geometric meshes;

FIG. 5 is a schematic three-dimensional view of a part of the lattice in FIG. 4;

FIG. 6 is a plane view of FIG. 5;

DETAILED DESCRIPTION OF A PREFERENTIAL FORM OF EMBODIMENT

Figure 7:
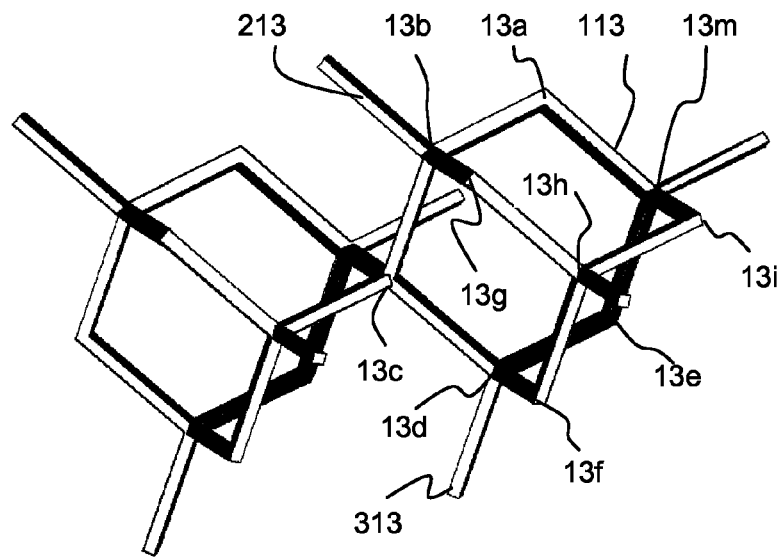
FIG. 7 shows the lattice of FIG. 4 in a different spatial orientation.

With reference to FIG. 1, a prosthetic element according to the present invention is indicated in its entirety by the reference number 10, and is usable for bone implant operations in the acetabular cavity of the hip.

Although in the description that follows we shall refer to the example of a spheroidal acetabular cup, it is understood that the invention can also be applied to other prosthetic element such as bone fillers, inserts, shells, etc.

The prosthetic element 10 comprises (FIGS. 1 and 2) a spheroidal cap 11 made of metal, which is internally hollow, so as to define an acetabular cup 11a in which a prosthetic head or an insert for an acetabular cup is accommodated, into which in turn the head of a femoral prosthesis is inserted.

According to a variant of the prosthetic element, not shown in the attached drawings, the cap 11 has a truncated cone shape.

In both cases, the cap 11 has an internal wall 16 made of compact material, with the shape of a semi-spherical cap or a truncated cone according to the two variants, but in any case mating with the shape of the acetabular seating 11a, which normally goes into contact with the prosthetic head or the insert for the acetabular cup.

Moreover, above the internal wall 16 (FIG. 1a), there is also an external part of the cap 11, shaped like a semi-spherical cap or a truncated cone, or other shapes, according to the possible variants, solid and in a single piece with the internal wall.

The external part of the cap 11 is formed by a three-dimensional lattice 12 with cells, as can be seen in the section in FIG. 1b, which ends at the bottom with a base layer 16a, typically an annular strip of material with denser or more compact cells, which connects directly to the internal wall 16, or is in physical continuity with the internal wall 16.

The internal wall 16 and the lattice 12 are solid, so as to form a single body and so as not to obtain a break in continuity between the two components of the cap 11, as will be clear from the following description of the method to make them.

This allows to guarantee mechanical continuity between the solid part of the cap 11 and the lattice part.

The lattice 12, in fact, is not an applied lining, and this prevents detachments of the porous part and possible galvanic effects between the regions of the implant having different density.

The three-dimensional lattice 12 has a pre-defined and desired thickness and has a cellular structure with open holes. The lattice 12 achieves a plurality of cavities 18, disposed three-dimensionally, open and intercommunicating, connected with each other. The lattice 12, furthermore, extends over all or part of the body of the prosthetic element 10, according to necessity.

The metal material used to make the prosthetic element 10 consists of a titanium alloy.

According to a preferential embodiment, the titanium alloy is the one called Ti6A14V, by virtue of its bio-compatibility properties.

According to a variant the metal material is based on a cobalt alloy.

According to one form of embodiment of the present invention, the prosthetic element 10 comprises constraint elements 14 suitable to be attached by means of pins or screws in the iliac wing. With reference to FIG. 3, the constraint elements 14 consist of a series of metal fins which protrude from the lower edge of the spheroidal cap 11, in a radial direction towards the outside. The metal fins are advantageously provided with one or more constraint holes 15 suitable for the insertion of an attachment pin or screw, not shown in the drawings, of the prosthetic element 10.

Constraint holes 17 are also provided on the surface of the lattice 12 of the cap 11. The constraint holes 17 are delimited by an annular perimeter 19 of compact material, and therefore not of the type with cavities 18, as in the rest of the lattice 12. The function of the annular perimeter 19 made of compact material is to reinforce attachment by means of the constraint holes 17.

The lattice 12 is characterized by a spatial repetition, for a pre-defined thickness, of a plurality of geometrical meshes 13 of polygonal shape the vertexes of which are not co-planar. This conformation defines in the structure of the body of the prosthetic element 10 the plurality of cavities 18.

In particular in FIG. 4, which shows as an example an advantageous model for osteo-integration, two meshes 13 are shown, respectively one with a continuous line, of vertexes 13a, 13b, 13c, 13d, 13e, 13f, 13g, 13h, 13i and 13m, and one in a discontinuous line, adjacent to each other.

According to a preferential embodiment, each of said geometric meshes 13 has a cellular geometry with elementary cells 13, open and contiguous, polygonal in shape, with vertexes that are not co-planar.

In particular, each mesh 13 is formed by a first part 113, all in all quadrangular in shape, having vertexes 13a, 13c, 13f and 13i, by a second part 213 with an angled segment of vertexes 13b, 13g and 13h, disposed transversely to the first part 113, substantially along a median line, and by a third part 313 with an angled segment of vertexes 13d, 13e and 13m, also disposed transversely to the first part 113, substantially along the other median line, in a cross with respect to the second part 213.

By angled segment we mean a segment consisting of several consecutive rectilinear segments with a different inclination, for example segments inclined alternatively upward and downward.

The four sides of the first part 113 in turn each consists of an angled segment, of which a first side 113a has a central vertex which coincides with the vertex 13b of the second part 213, a second side 113b which has a central vertex that coincides with the vertex 13d of the third part 313, a third side 113c which has a central vertex that coincides with the vertex 13h of the second part 213, and finally a fourth side 113d which has a central vertex that coincides with the vertex 13m of the third part 313.

The random spatial repetition of the mesh 13 defines a hexagonal geometry of which FIGS. 5 and 6 indicate for example a hexagon 413, having vertexes 13a, 13m, 13i, 13h, 13g, 13b.

To visualize the hexagons thus defined, one starts from one of the vertexes 13a, 13c, 13f or 13i, one continues, passing through one of the central vertexes 13m, 13h, 13d, 13b, along the first part 113 toward one of the other four opposite central vertexes 13i, 13f, 13c or 13a. For example, starting from the vertex 13a, one continues passing through the central vertex 13m, to the vertex 13i.

Afterwards, to visualize the hexagon, one continues without turning back along a segment already traveled, as far as one of the central vertexes 13h, 13d, 13b or 13m. for example, from the vertex 13i one continues to vertex 13h.

From here, passing on one of the two parts 213 or 313, one continues to the central vertex on the opposite side 13b, 13d, 13h or 13m, always passing either through the vertex 13g or through vertex 13e respectively of part 213 or 313. For example, from vertex 13h, one goes to the opposite vertex 13b, passing through vertex 13g. The hexagon will have a three-dimensional conformation disposed on various planes, with at least one of its vertexes not co-planar with the others. In the case of the hexagon 413, we have three planes, so as to have two vertexes 13a and 13h which are not co-planar. That is, we have two end planes facing in opposite directions, and a central plane transverse to the two end planes. For the hexagon 413 defined by the vertexes 13a, 13m, 13i, 13h, 13g and 13b, we will have a first plane on which the vertexes 13a, 13b and 13m lie, a transverse plane on which the vertexes 13m, 13i, 13g and 13b lie, and a second plane on which the vertexes 13g, 13h and 13i lie. In this case, the first plane faces up and the second plane faces down.

Therefore, each of the meshes 13 defines all in all four hexagons, one for each vertex 13a, 13c, 13f and 13i, to which the reference number 413 is assigned for convenience, in the space, with the conformation described above.

Figure 8:
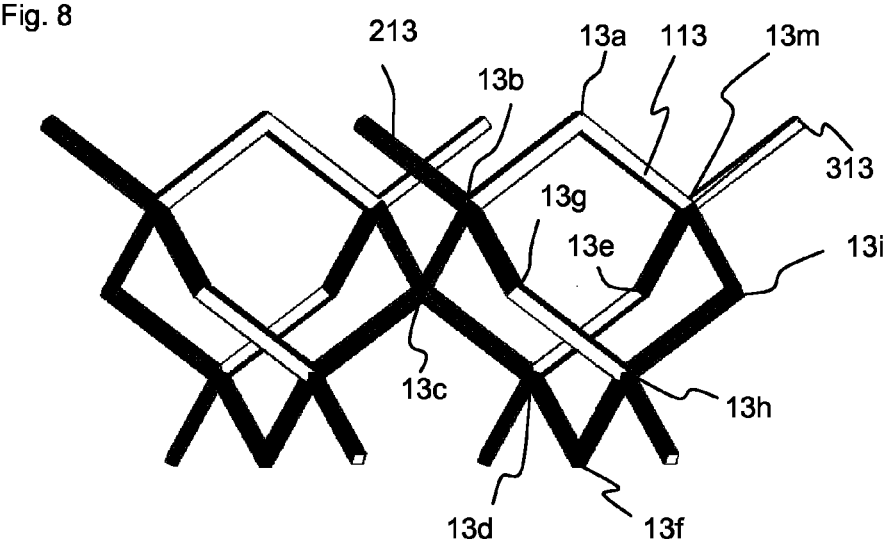
FIG. 8 shows the lattice of FIG. 4 in another different spatial orientation.

FIG. 7 shows FIG. 4 in a different spatial orientation. FIG. 8 shows FIG. 4 in another different spatial orientation. FIGS.

7 and 8 further illustrate the eight rectilinear parts of the first part of the mesh and the hexagons formed by the first part 113 with the second part 213 as well as the hexagons formed by the first part 113 with the third part 313.

Figure 9:
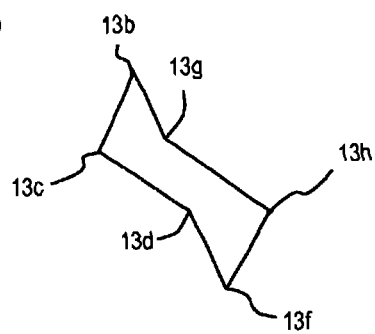
FIG. 9 shows a second hexagon formed by intersection of a first part and a second part of the lattice in the orientation of FIG. 8.
Figure 10:
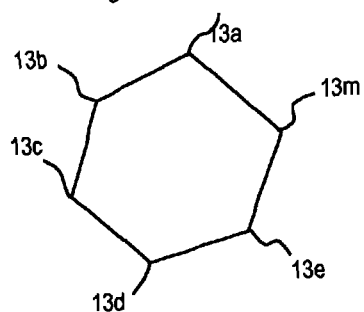
FIG. 10 shows a first hexagon formed by intersection of the first part and a third part of the lattice in the orientation of FIG. 7.
Figure 11:
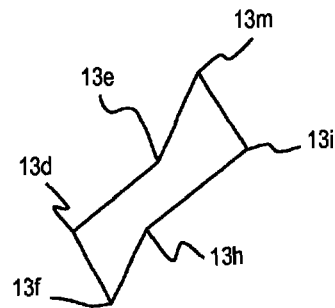
FIG. 11 shows a second hexagon formed by intersection of the first part and the third part of the lattice in the orientation of FIG. 8.

FIGS. 9, 10 and 11 further illustrate hexagons of a lattice of the mesh of FIG. 4.

FIG. 9 shows a second hexagon formed by intersection of the first part 113 and the second part 213 having vertices 13b, 13c, 13d, 13f, 13h and 13g in the orientation of FIG. 8.

FIG. 10 shows a first hexagon formed by intersection of the first part 113 and the third part 313 having vertices 13a, 13m, 13e, 13d, 13c and 13b in the orientation of FIG. 7.

FIG. 11 shows the second hexagon formed by intersection of the first part 113 and the third part 313 having vertices 13m, 13i, 13h, 13f, 13d and 13e in the orientation of FIG. 8.

The sections of the contiguous elementary cells delimited by the meshes 13 have a plane surface 403 with an area equal to the area of a circle with an equivalent diameter comprised in a range that goes from about 0.3 mm to about 1.5 mm. A value of this equivalent diameter that supplies optimum sizes of the peripheral cellular structure is in the range of about 0.6 mm. This optimum diameter determines a minimized plane surface that guarantees both bone re-growth and the anchorage of the prosthesis, and also an optimized bulk of the lattice 12, in the light of the constraints of size and design imposed by the size of the patient's bones, in particular of the hip.

Therefore, both the cellular conformation of the prosthetic element 10 and the lattice 12, and also the size and shape of the cavities 18, confer on the surface structure of the prosthetic element 10 a peculiar property of porosity. This porosity promotes, after the implant operation, both the anchorage of the prosthesis and the re-growth of the bone tissue that is in direct contact with the prosthetic element 10, increasing and accelerating the process of osteo-integration.

According to the present invention, the method to make the prosthetic element 10 comprises a first step in which, by means of three-dimensional modeling programs for electronic processors, a model of the prosthetic element 10 is generated. Always using the modeling programs, the model is divided into a multiplicity of plane sections with a limited and determinate thickness. The plane sections define the sequence of plane portions intended to be deposited in sequence by means of powdered metal material.

In a second step, by means of the Electron Beam Melting technique, the prosthetic element 10 is made. In a preferential embodiment it is provided to melt, in conditions of high vacuum, using an apparatus suitable for EBM, a bath of powders, of the desired granulometry, of metal material by means of a beam of high-speed electrons, in the range of half the speed of light. The powders of metal material of the desired granulometry are deposited in successive layers in the desired place and in the desired sequence and defined in the modeling step, and made to melt in order to form the prosthetic element 10 according to the present invention, in particular the cap 11, including the internal wall 16, the external wall formed by the lattice 12, and the base layer 16a.

In other words, the material is melted gradually, thus making the internal wall 16 and the lattice 12 wall simultaneously.

If construction is started from the base, we will have various cross sections of the cap 11 as we go up, initially consisting of annular layers formed of compact material, which form the base layer 16a and subsequently other annular layers, of a suitable diameter going upward, which consist, like a single piece, of a portion of compact material, towards the inside, to define the internal wall 16, and a lattice portion, towards the outside, to define the lattice 12.

It is clear that in the present description we use the term "portion" for convenience, but this should not be taken to mean that they are two separate bodies joined together afterward; on the contrary, it is the same body having parts with different morphological properties (compact material on one side, lattice on the other).

The summation, on the height, of the compact portions will form the internal wall 16 made of compact material, whereas the combination of lattice portions defines, at the end of the process, the external lattice 12 proper.

The desired curvature of the internal wall 16 and of the mating lattice 12 is determined by said geometric variation in the layers that are gradually made.

In said second step the lattice 12 is defined in its periphery as an open and desired cellular structure, so as to make the prosthetic element 10 with a plurality of compartments equivalent to cylinders with a diameter comprised in the range from about 0.3 mm to about 1.5 mm. A preferential value of the diameter is around 0.6 mm.

The EBM technique used in the second step can be replaced by an equivalent technique, for example the technique known as DMSLS (Direct Metal Selective Laser Sintering), where the bath of powders is melted by a high power laser ray.

The metal powders used in the second step are preferably based on titanium or one of its alloys, such as for example the alloy Ti6A14V, or a cobalt based alloy.

It is clear that modifications and/or additions of parts and/or steps may be made to the prosthetic element with cellular structure and the method to make a prosthetic element with cellular structure according to the present invention as described heretofore, without departing from the field and scope of the present invention.

For example, the base layer 16a is made of compact material or in a dense cell structure, where by compact material we also mean a material formed by dense cells, whose equivalent diameter tends toward zero.

The internal wall 16 can also be with a lattice structure similar to the lattice 12, or with a cell structure, as well as of compact material.

In another form of embodiment, the holes 15 on the fins 14 of the cap 11 comprise a crown made of compact material, or dense cells.

It is also clear that, although the present invention has been described with reference to specific examples, a person of skill in the art shall certainly be able to achieve many other equivalent forms of prosthetic element with cellular structure and the method to make a prosthetic element with cellular structure, having the characteristics as set forth in the claims and hence all coming within the field of protection defined thereby.

The invention claimed is:

1. A prosthetic device comprising:
   a body;
   a cap made of metal material, having inside an acetabular seating,
   said cap having an internal wall that lines the seating and an external part consisting of a lattice with cells making a plurality of cavities disposed three-dimensionally, open and intercommunicating, connected with each other,
   said lattice being solid with the external part facing toward the outside of the internal wall,
   at least part of the lattice is formed, without a break in continuity, by a plurality of geometric meshes of polygonal shape repeated in space over all or part of the body, having a cellular geometry with elementary cells open and contiguous, to define a plurality of polygons with a spatial development delimiting the cavities, so the lattice is able to promote osteo-integration, wherein each geometric mesh is formed by a first polygonal part with four sides, each of said four sides formed as an angled segment, and a second part formed as an angled segment and a third part formed as an angled segment, wherein each angled segment has first and second consecutive rectilinear segments, wherein an angle is formed in the angled segment at an intersection of each pair of its first and the second consecutive segments; wherein the first polygonal part has vertexes that are not co-planar;

the second and the third part with angled segments are disposed transversely to the first part substantially across a respective median line of the first part, crossed with respect to each other, superimposed on the first polygonal part, one on one side and one on the other side to define in the space a plurality of hexagons having vertexes that are not co-planar, the first part and the second part forming a first hexagon and a second hexagon of said plurality of hexagons having vertexes that are not co-planar; the first part and the third part forming a third hexagon and a fourth hexagon of said plurality of hexagons having vertexes that are not co-planar;

wherein a first end of a first angled segment of the second part coincides with a first vertex of the first part and a second end of a second angled segment of the second part coincides with a second vertex of the first part; and wherein a first end of a first angled segment of the third part coincides with a third vertex of the first part and a second end of a second angled segment of the third part coincides with a fourth vertex of the first part.

2. The prosthetic device as in claim 1, wherein the internal wall is made of compact material.

3. The prosthetic device as in claim 1, wherein the lattice has at a lower part a compact base layer, in physical continuity with the internal wall.

4. The prosthetic device as in claim 1, wherein the geometric meshes all have the same shape and size, varying their disposition in the lattice, wherein the first part has eight said rectilinear segments.

5. The prosthetic device as in claim 1, wherein the first polygonal part is substantially quadrangular.

6. The prosthetic device as in claim 1, wherein each geometric mesh defines four hexagons with a spatial development.

7. The prosthetic device as in claim 1, wherein said metal material is titanium based.

8. The prosthetic device as in claim 7, wherein said metal material is an alloy Ti6A14V.

9. The prosthetic device as in claim 1, wherein said metal material consists of a cobalt alloy.

10. The prosthetic device as in claim 1, wherein said cap has a spheroidal shape.

11. The prosthetic device as in claim 1, wherein the cap has a plurality of holes which are delimited along the perimeter by a portion made of compact material.

12. A method to make a prosthetic element comprising:
a body;
a cap made of metal material, having inside an acetabular seating,
said cap having an internal wall that lines the seating and an external part consisting of a lattice with cells making a plurality of cavities disposed three-dimensionally, open and intercommunicating, connected with each other,
said lattice being solid with the external part facing toward the outside of the internal wall,
at least part of the lattice is formed, without a break in continuity, by a plurality of geometric meshes of polygonal shape repeated in space over all or part of the body, having a cellular geometry with elementary cells open and contiguous, to define a plurality of polygons with a spatial development delimiting the cavities, so the lattice is able to promote osteo-integration, wherein each geometric mesh is formed by a first polygonal part with four sides, each of said four sides formed as an angled segment, and a second part formed as an angled segment and a third part formed as an angled segment, wherein each angled segment has first and second consecutive rectilinear segments, wherein an angle is formed in the angled segment at an intersection of each pair of its first and the second consecutive segments; wherein the first polygonal part has vertexes that are not co-planar;

the second and the third part with angled segments are disposed transversely to the first part substantially across a respective median line of the first part, crossed with respect to each other, superimposed on the first polygonal part, one on one side and one on the other side to define in the space a plurality of hexagons having vertexes that are not co-planar, the first part and the second part forming a first hexagon and a second hexagon of said plurality of hexagons having vertexes that are not co-planar; the first part and the third part forming a third hexagon and a fourth hexagon of said plurality of hexagons having vertexes that are not co-planar;

wherein a first end of a first angled segment of the second part coincides with a first vertex of the first part and a second end of a second angled segment of the second part coincides with a second vertex of the first part; and wherein a first end of a first angled segment of the third part coincides with a third vertex of the first part and a second end of a second angled segment of the third part coincides with a fourth vertex of the first part;

the method comprising:
making successive, continuous, parallel, adjacent and solid layers to constitute an internal wall of the cap that lines the seating and in physical continuity with every single layer at least part of the external part of the cap, wherein the layers that make up the external part are coordinated in relation to a pre-determined final figure, wherein said plurality of layers is obtained in a discontinuous form to determine a lattice with cells achieving a plurality of cavities disposed three-dimensionally, open and intercommunicating, connected with each other, the lattice being made in physical continuity with the part facing toward the outside of the internal wall.

13. The method as in claim 12, wherein the internal wall is made of compact material.

14. The method as in claim 12, wherein a base layer of compact cells is obtained.

15. The method as in claim 12, wherein said step of making successive layers is obtained using the EBM (Electron Beam Melting) technique.

16. The method as in claim 12, wherein said step of making successive layers is obtained using the DMSLS (Direct Metal Selective Laser Sintering) technique.

17. The method as in claim 12, wherein in said step of making the individual layers, said lattice is defined in the periphery thereof as an open and desired cellular structure, to make the geometric meshes with a cellular geometry with open and contiguous elementary cells of a polygonal shape with vertexes that are not co-planar, wherein the open free area of each elementary cell has an equivalence to a circle with a diameter comprised in a range from about 0.3 mm to about 1.5 mm.

18. The method as in claim 17, wherein said diameter is around 0.6 mm.

19. The method as in claim 12, wherein metal powders of desired granulometry are used, said powders being fixed in the desired place and in the desired sequence, layer by layer, to create the desired lattice.

20. The method as in claim 19, the powder used is titanium based.

21. The method as in claim 20, wherein the powder used is the titanium alloy TI6A14V.

22. The method as in claim 19, wherein the powder used is a cobalt alloy.

23. The prosthetic device as in claim 1,
wherein the second part has an intermediate vertex between said first and second ends of said second part and the third part has an intermediate vertex between said first and second ends of said third part,
wherein the second part intermediate vertex does not coincide with the third part intermediate vertex.

24. The prosthetic device as in claim 23, wherein the second part does not contact the third part.

\* \* \* \* \*